(12) United States Patent
Pellerin De Beauvais

(10) Patent No.: US 11,717,146 B2
(45) Date of Patent: Aug. 8, 2023

(54) LARYNGOSCOPE SYSTEM AND BLADE ASSEMBLY

(71) Applicant: COMEPA INDUSTRIES LIMITED, Hong Kong (CN)

(72) Inventor: Gilles Pellerin De Beauvais, Hong Kong (CN)

(73) Assignee: COMEPA INDUSTRIES LIMITED, Hong Kong (CN)

(*) Notice: Subject to any disclaimer, the term of this patent is extended or adjusted under 35 U.S.C. 154(b) by 321 days.

(21) Appl. No.: 16/956,780

(22) PCT Filed: Dec. 28, 2018

(86) PCT No.: PCT/CN2018/125081
§ 371 (c)(1),
(2) Date: Jun. 22, 2020

(87) PCT Pub. No.: WO2019/129250
PCT Pub. Date: Jul. 4, 2019

(65) Prior Publication Data
US 2020/0315443 A1    Oct. 8, 2020

(30) Foreign Application Priority Data
Dec. 28, 2017 (EP) .................................... 17306957

(51) Int. Cl.
*A61B 1/267*    (2006.01)
*A61B 1/00*    (2006.01)
(Continued)

(52) U.S. Cl.
CPC .......... *A61B 1/267* (2013.01); *A61B 1/00052* (2013.01); *A61B 1/00066* (2013.01);
(Continued)

(58) Field of Classification Search
CPC . A61B 1/267; A61B 1/00052; A61B 1/00066; A61B 1/00105
(Continued)

(56) References Cited

U.S. PATENT DOCUMENTS 2,070,820 A * 2/1937 Allyn ..................... A61B 1/267
                                                    600/196
4,273,112 A * 6/1981 Heine ................ A61B 1/00032
                                                    600/199

(Continued)

FOREIGN PATENT DOCUMENTS

CH       710367 A2    5/2016
CN     102068230 A    5/2011
(Continued)

OTHER PUBLICATIONS

International Search Report and Written Opinion dated Apr. 9, 2019 in corresponding application No. PCT/CN2018/125081; 9 pgs.

*Primary Examiner* — John P Leubecker
*Assistant Examiner* — Jae Woo
(74) *Attorney, Agent, or Firm* — Maier & Maier, PLLC

(57) ABSTRACT

A laryngoscope system including a laryngoscope device and a blade assembly. The laryngoscope device has a handle member and a front-end member, which includes: a longitudinal member, with a channel, being connected with the handle member; a sliding part having at a distal end an imaging and/or a lighting device and being configured to be at least partially inserted in and movable along the channel, which has an abutment and a positioning spring between the abutment and a proximal end of the sliding part. The blade assembly is configured to cooperate with the front-end member and has fixed to one another: a blade having a distal tip; an insertion housing, which has a cavity to receive the front-end member, includes an engaging element having an edge to cooperate with the longitudinal member's distal end, (Continued)

the engaging element's edge being positioned at a predefined distance from the blade's distal tip.

13 Claims, 7 Drawing Sheets

(51) Int. Cl.
    *A61B 1/012*     (2006.01)
    *A61B 1/06*     (2006.01)
    *A61M 16/04*     (2006.01)

(52) U.S. Cl.
    CPC .......... *A61B 1/00105* (2013.01); *A61B 1/012* (2013.01); *A61B 1/0676* (2013.01); *A61M 16/0488* (2013.01)

(58) Field of Classification Search
    USPC ........................................................ 600/190
    See application file for complete search history.

(56) References Cited

U.S. PATENT DOCUMENTS

| | | | | |
|---|---|---|---|---|
| 4,320,745 | A * | 3/1982 | Bhitiyakul | A61B 1/267 600/188 |
| 4,360,008 | A * | 11/1982 | Corazzelli, Jr. | A61B 1/267 600/197 |
| 4,573,451 | A * | 3/1986 | Bauman | A61B 1/267 600/190 |
| 4,679,547 | A * | 7/1987 | Bauman | A61B 1/267 600/198 |
| 4,947,829 | A | 8/1990 | Bullard | |
| 5,498,231 | A * | 3/1996 | Franicevic | A61B 1/267 128/207.14 |
| 5,542,905 | A * | 8/1996 | Nussenbaum | A61B 1/00032 600/185 |
| 5,772,581 | A * | 6/1998 | Gaines | A61B 1/00105 600/199 |
| 6,036,639 | A * | 3/2000 | Allred, III | A61B 1/00032 600/199 |
| 6,139,491 | A * | 10/2000 | Heine | A61B 1/07 600/199 |
| 6,217,514 | B1 * | 4/2001 | Gruen | A61B 1/267 600/185 |
| 6,251,069 | B1 * | 6/2001 | Mentzelopoulos | A61B 1/267 600/196 |
| 6,277,068 | B1 * | 8/2001 | Wojnowicz | A61B 1/267 600/199 |
| 8,414,481 | B2 * | 4/2013 | Hakanen | A61B 1/267 600/196 |
| 9,924,858 | B2 * | 3/2018 | Miller | A61B 1/267 |
| 9,993,148 | B2 * | 6/2018 | Vasan | A61B 17/02 |
| 10,039,444 | B1 * | 8/2018 | Ghorbanian | A61B 1/267 |
| 2006/0276693 | A1 * | 12/2006 | Pacey | A61B 1/267 600/188 |
| 2010/0036204 | A1 * | 2/2010 | Anders | A61B 1/0011 600/190 |
| 2010/0041952 | A1 * | 2/2010 | Castellucci | A61B 1/00165 600/121 |
| 2010/0312059 | A1 | 12/2010 | McGrath | |
| 2011/0254938 | A1 * | 10/2011 | Asada | A61B 1/05 348/76 |
| 2012/0178997 | A1 * | 7/2012 | Tydlaska | A61B 1/267 600/188 |
| 2013/0060089 | A1 * | 3/2013 | McGrath | A61B 1/267 600/187 |
| 2013/0184527 | A1 * | 7/2013 | Castellucci | A61B 1/00135 600/121 |
| 2013/0190568 | A1 * | 7/2013 | Hakanen | A61B 1/06 600/199 |
| 2014/0107422 | A1 * | 4/2014 | Huels | A61B 1/00105 600/188 |
| 2015/0112146 | A1 | 4/2015 | Donaldson | |
| 2016/0051781 | A1 * | 2/2016 | Isaacs | A61B 1/00066 600/188 |
| 2016/0128548 | A1 * | 5/2016 | Lai | A61B 1/267 600/188 |
| 2016/0206188 | A1 * | 7/2016 | Hruska | A61B 1/06 |
| 2016/0242637 | A1 * | 8/2016 | Tydlaska | A61B 1/00052 |
| 2018/0228360 | A1 * | 8/2018 | Shu | A61B 1/05 |
| 2019/0142262 | A1 * | 5/2019 | Inglis | A61B 1/00048 600/188 |
| 2020/0138282 | A1 * | 5/2020 | Benuri-Silbiger | A61B 1/267 |
| 2020/0288961 | A1 * | 9/2020 | Elbaz | A61B 1/00128 |
| 2020/0297452 | A1 * | 9/2020 | Coppedge | A61B 1/317 |
| 2022/0000354 | A1 * | 1/2022 | Stoffel | A61B 1/126 |
| 2022/0218187 | A1 * | 7/2022 | Bendory | A61B 1/00042 |

FOREIGN PATENT DOCUMENTS

| | | |
|---|---|---|
| CN | 102481086 A | 5/2012 |
| CN | 203169136 U | 9/2013 |
| CN | 105595952 A | 5/2016 |

* cited by examiner

LARYNGOSCOPE SYSTEM AND BLADE ASSEMBLY

FIELD

The present invention relates to a laryngoscope system comprising a laryngoscope device and a blade assembly. The invention also relates to a blade assembly for a laryngoscope device.

BACKGROUND

In general, a laryngoscope is a medical device used for endotracheal intubation to maintain the respiration tract of a subject. A laryngoscope ensures the free airway of a subject during intubation. A laryngoscope comprises an elongate member configured to extend in the oral cavity of a subject during intubation. A laryngoscope typically comprises a handle which is usually elongate and which may be arranged at an angle to the proximal end of the elongate member. The elongate member comprises an interchangeable blade which may have a straight or curved design. The use of one or another design depends on the anatomy of the subject.

A laryngoscope can include an imaging device within the elongate member, which is usually placed in the proximity of the working end of the blade. The imaging device may be part of the elongate member or of the body of the laryngoscope. These devices are largely used since they provide the medical professionals with a clear view of the tracheal anatomy of a subject. Images may be displayed on a monitor directly coupled to the laryngoscope or on a display operationally connected to the laryngoscope. Laryngoscopes further reduce the risk of injury to a subject's soft tissues, making it possible for the physician to steer the tubing without causing injured areas.

Devices have been disclosed in the prior art that relate to laryngoscopes. One example of laryngoscope is disclosed in US 2010/312059. US 2010/312059 discloses a laryngoscope comprising a handle, an insertion section, which comprises a tube guide for retaining and guiding an endotracheal tube during intubation, and a display screen for displaying images received from a video camera which is located within or attached to the insertion section. However, the handle and the video camera are configured to be used with a unique blade size.

US 2015/112146 discloses a laryngoscope having a repositionable display screen, and removable blade members of various sizes. The display screen is moveably connected to a fiber optic camera through a fiber optic cable, which runs through the handle and is inserted through an aperture in the blade. The fiber optic camera at the free end of the cable is positioned in the environment near the working end of the blade member during a laryngoscopy procedure. However, the positioning of the camera relies on the user, therefore the quality of the image will be impacted by the skill level of the user.

There is a need to avoid relying on a user skill level to adapt the positioning of the imaging device or other lighting device of a laryngoscope when different blade sizes are used.

More particularly, there is a need for a simple and effective mechanism allowing the positioning of the imaging device or lighting device of a laryngoscope at various fixed positions according to the size of the blade that is used.

SUMMARY

To this end, the present invention relates to a laryngoscope system, comprising:

a laryngoscope device comprising:
  a handle member;
  a front-end member protruding from a proximal end of the handle member, wherein the front-end member comprises:
    a longitudinal member connected with the handle member, the longitudinal member comprising a channel extending from the handle member to a distal end of the longitudinal member;
    a sliding part comprising at a distal end an imaging device and/or a lighting device, the sliding part being configured to be at least partially inserted in the channel and movable along said channel;
    the channel comprising an abutment and a positioning spring between said abutment and a proximal end of the sliding part;
a blade assembly configured to cooperate with the front-end member of the laryngoscope device, the blade assembly comprising, fixed to one another:
  a blade comprising a distal tip;
  an insertion housing comprising a cavity configured to receive the front-end member of the laryngoscope device;
  wherein the insertion housing includes an engaging element having an edge configured to cooperate with the distal end of the longitudinal member, the edge of the engaging element being positioned at a predefined distance from the distal tip of the blade.

Thanks to the invention, there is an automatic displacement of the imaging device or lighting device of the laryngoscope device towards a position in accordance with the size of the blade, at the predefined distance from the distal tip of the blade, which is a constant, so that a clear view of the larynx is obtained independently from the selected blade size.

Within the frame of the invention, when the sliding part of the laryngoscope device comprises a lighting device at its distal end, the lighting device positioned at the distal end may be a light source, or a lighting device remote from a light source, such as an end of an optical fiber in which light is injected for example by a light source positioned in the handle member of the laryngoscope device.

In the assembled configuration of the laryngoscope device and the blade assembly, the edge of the engaging element receives the distal end of the sliding part in abutment against the force generated by the positioning spring. This ensures an automatic positioning of the imaging device or lighting device present at the distal end of the sliding part at the predefined distance from the distal tip of the blade.

In one embodiment, the sliding part of the laryngoscope device comprises an imaging device at its distal end, and the predefined distance between the engaging element and the distal tip of the blade corresponds to an optimized field of view of the imaging device.

In one embodiment, the engaging element is transparent so that the imaging device or lighting device of the laryngoscope device can operate through the engaging element.

In one embodiment, the laryngoscope system comprises at least two blade assemblies having blades of different lengths. In this way, the laryngoscope system can comprise a unique laryngoscope device configured to cooperate with several blade assemblies having blades of different lengths.

In one embodiment, for the at least two blade assemblies, the predefined distance between the engaging element and the distal tip of the blade is the same, independently from the length of the blade.

In one embodiment, the insertion housing of the blade assembly comprises retaining means configured to cooperate with a retaining mechanism of the laryngoscope device so as to lock the blade assembly with respect to the laryngoscope device.

In one embodiment, the retaining mechanism of the laryngoscope device comprises a follower movable so as to lock and unlock the blade assembly with respect to the laryngoscope device. In particular, the follower is movable between a locking position, in which the follower locks the blade assembly with respect to the laryngoscope device, and an unlocking position, in which the follower unlocks the blade assembly with respect to the laryngoscope device, the transition between the locking position and the unlocking position of the follower being activated by a mechanical interface.

In one embodiment, a movement of the mechanical interface in a first direction induces a movement of the follower in a second direction perpendicular to the first direction.

In one embodiment, the sliding part of the laryngoscope device comprises an imaging device at its distal end, the laryngoscope system further comprising a display screen assembled to a distal end of the handle member and connected to the imaging device.

In one embodiment, the blade and the insertion housing of the blade assembly are fixed to one another by means of fastening means configured to block at least one degree of freedom of the blade relative to the insertion housing.

The present invention also relates to a blade assembly for a laryngoscope device adapted to be introduced in the mouth of a subject, wherein the blade assembly comprises, fixed to one another:
a blade comprising a distal tip,
an insertion housing comprising a cavity configured to receive a front-end member of a laryngoscope device, wherein the insertion housing comprises an engaging element having an edge configured to cooperate with the distal-end of the front-end member of the laryngoscope device, the edge of the engaging element being positioned at a predefined distance from the distal tip of the blade.

In one embodiment, the predefined distance between the engaging element and the distal tip of the blade corresponds to an optimized field of view of an imaging device of the laryngoscope device.

In one embodiment, the engaging element is transparent.

In one embodiment, the blade is made of, or comprises, a metal, such as stainless steel. Selecting a metallic material for the blade is advantageous in that a high mechanical resistance of the blade is obtained even for a low thickness of the blade. It is thus possible to have a thin blade, which is less invasive for the subject.

In one embodiment, the insertion housing is made of a transparent material, in particular a transparent plastic (or polymer) material. In a particular embodiment, the insertion housing is made of a disposable plastic (or polymer) material.

In one embodiment, the blade and the insertion housing are fixed to one another by means of fastening means configured to block at least one degree of freedom of the blade relative to the insertion housing.

In the present invention, the following terms have the following meanings:

"As used herein the singular forms "a", "an", and "the" include plural reference unless the context clearly dictates otherwise.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably of 5 percent.

"Blade" refers to a part of a laryngoscope which is configured to be introduced into the mouth of a subject.

"Field of view" refers to a solid angle through which a detector is sensitive to electromagnetic radiation.

"Laryngoscope" refers to a tubular endoscope that is inserted into the larynx through the mouth and used to observe the interior of the larynx.

"Subject" refers to a mammal, preferably a human. Within the meaning of the present invention, a subject may be a patient, i.e. a person receiving medical attention, undergoing or having underwent a medical treatment, or monitored for the development of a disease.

DETAILED DESCRIPTION

The following detailed description will be better understood when read in conjunction with the drawings. For the purpose of illustrating, the device is shown in preferred embodiments. It should be understood, however that the application is not limited to the precise arrangements, structures, features, embodiments, and aspects shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

The present invention relates to a laryngoscope system comprising both a blade assembly and a laryngoscope device. The invention also relates to a blade assembly for a laryngoscope device. In order to better understand the present invention, the two components of the laryngoscope system will be described.

Figure 1:
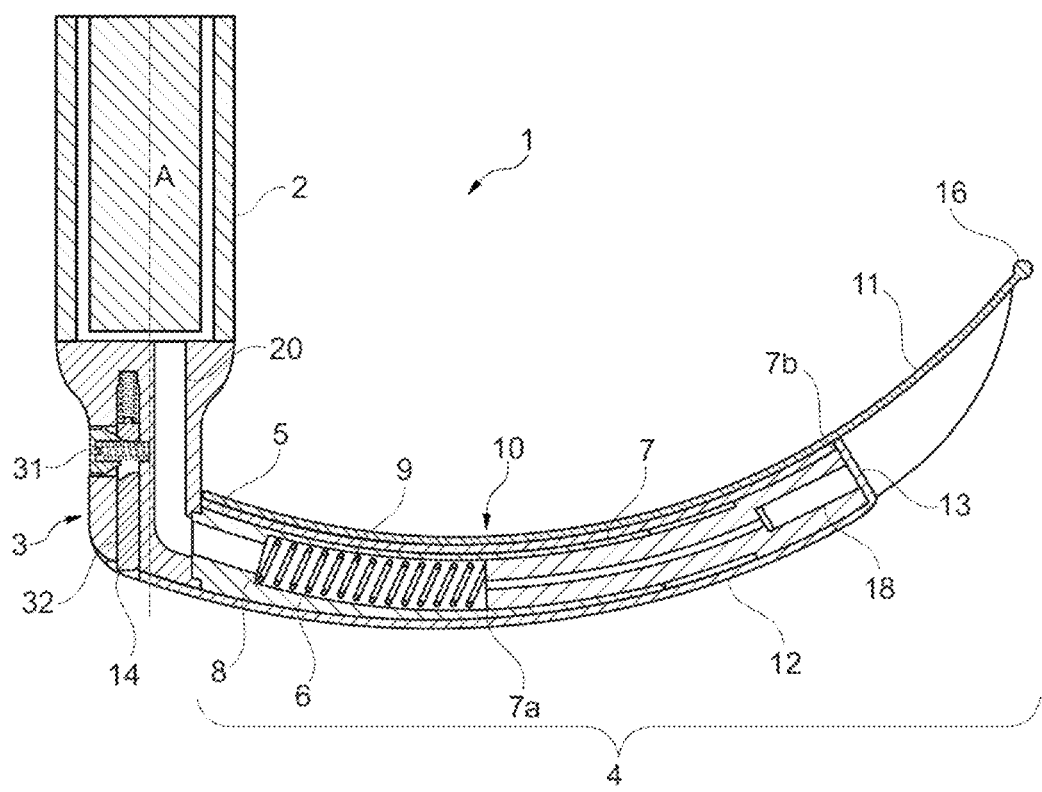
FIG. 1 is a partial cross section of a laryngoscope system comprising a laryngoscope device and a blade assembly, according to one embodiment of the present invention.
Figure 2:
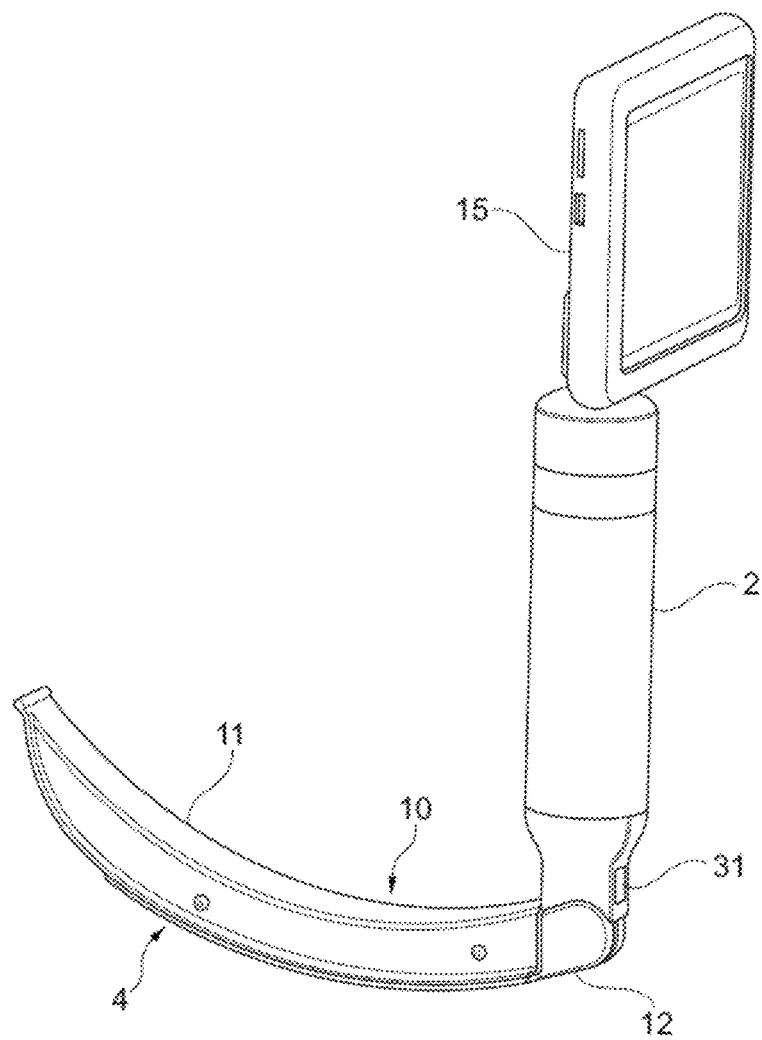
FIG. 2 is a perspective view of the laryngoscope system of FIG. 1.

The blade assembly 10 comprises an insertion housing 12, at least one engaging element 13, a complementary retaining means 14 and a blade 11, as shown in FIGS. 1 and 2.

As shown in the figures, the insertion housing 12 comprises a cavity 121 configured to house the front-end member 4 of a laryngoscope device 1. According to the embodiment illustrated in the figures, the insertion housing 12 comprises four walls forming a frame, the cross section defined by the inner walls of the frame being substantially equal to that of the front-end member 4. The insertion housing 12 has a first end and a second end. The insertion housing 12 comprises an engaging means 13 having an edge adapted to cooperate with the distal end of the laryngoscope device 1. The edge forms a first plane, and the distal end of the laryngoscope device forms a second plane. The first plane and the second plane are in contact in order to cooperate together. The edge is able to engage with the second plane by forming a contact plane against the distal end of the laryngoscope device. According to one embodiment, the engaging element 13 is disposed on the second end of the insertion housing 12. On the other side of the insertion housing 12, the first end of the insertion housing 12 comprises an opening through which the front-end member 4 of the laryngoscope device 1 may be inserted.

The engaging element 13 comprises a plurality of stops homogenously distributed on the second end of the insertion housing 12 so as to surround the front-end member 4 of the laryngoscope device 1. In the embodiment shown in the figures, the engaging element 13 is a surface extending between the walls of the insertion housing frame.

According to one embodiment, the insertion housing 12 is made of a disposable plastic material known by those skilled in the art. The disposable plastic material may be transparent or not. Preferably, the engaging element 13 is transparent.

Figure 7:
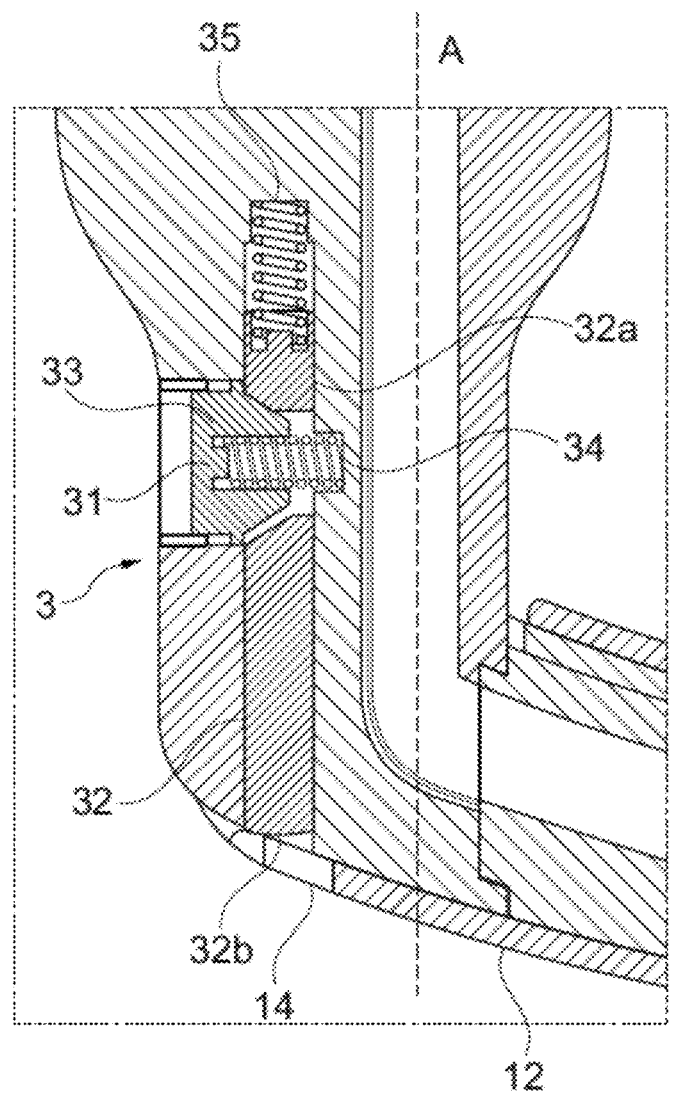
FIG. 7 is a cross section at a larger scale of part of the laryngoscope system of FIG. 1, showing the blade assembly connected to the retaining mechanism of the laryngoscope device in an unlocked configuration.
Figure 8:
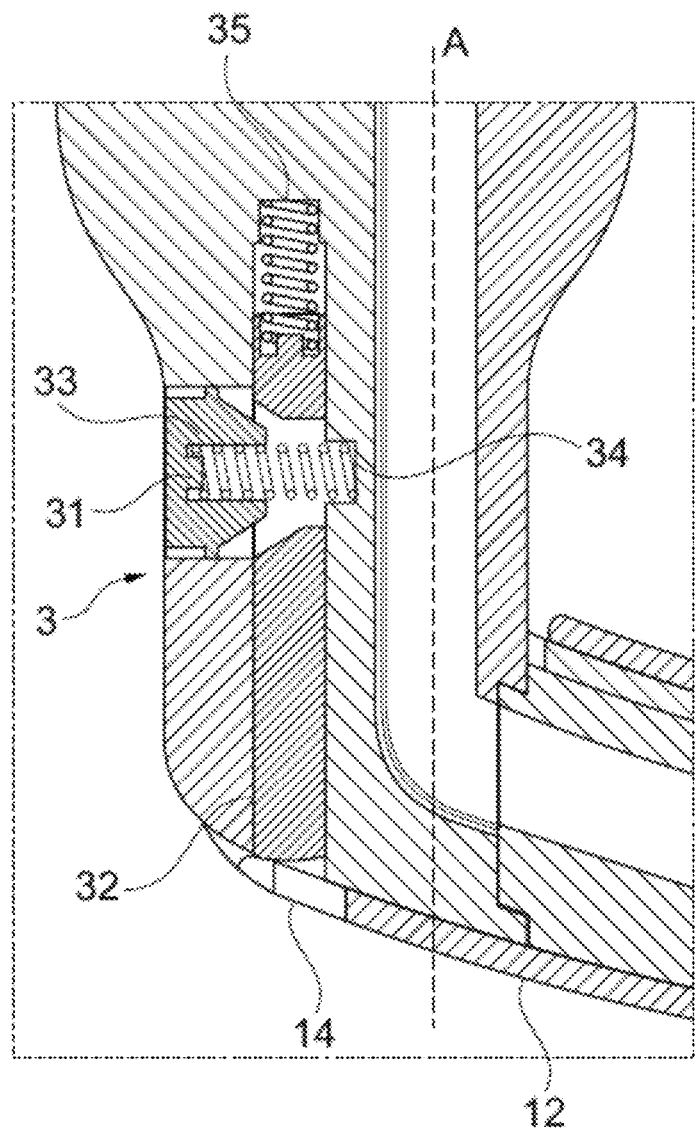
FIG. 8 is a cross section similar to FIG. 7, showing the blade assembly connected to the retaining mechanism of the laryngoscope device in a locked configuration.

The complementary retaining means 14 of the insertion section 12 is configured to cooperate with a retaining mechanism 3 of the laryngoscope device 1 so as to lock the insertion housing 12 with respect to the laryngoscope device 1. According to one embodiment, the complementary retaining means 14 is a recess or a through hole in the insertion housing 12, as shown in FIGS. 1, 7 and 8. In this case, the through hole cooperates with a protrusion or a pin of the retaining mechanism 3 of the laryngoscope device 1. According to another embodiment, the complementary retaining means 14 is protrusion or a pin. In this case, the pin or the protrusion cooperates with a hole or a cavity of the retaining mechanism 3 of the laryngoscope device 1.

As shown in FIGS. 1 to 3, 5 and 6, the blade assembly 10 comprises a blade 11 extending longitudinally along the insertion housing 12 and terminating at a distal tip 16. The blade 11 is adapted to be inserted in the oral cavity of a subject, in order to hold the tracheal passage open and permit the insertion of a length of tubing.

Figure 6:
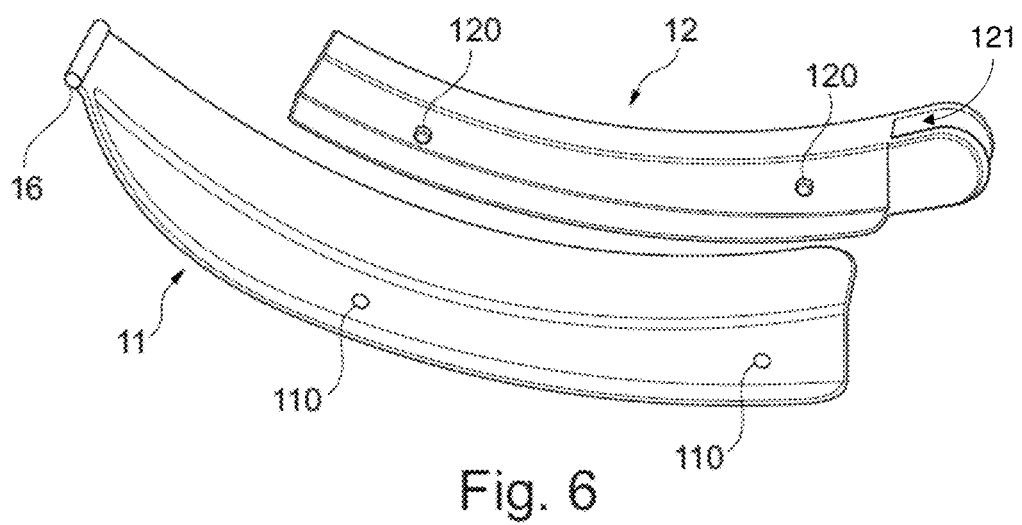
FIG. 6 is an exploded perspective view of the blade assembly of FIG. 5.

The blade assembly 10 comprises a fixation for fastening the insertion housing 12 and the blade 11 together, with reference to FIG. 6. Said fixation is configured to block at least one degree of freedom of the blade 11 relative to the insertion housing 12. The fixation may be obtained by the cooperation of blocking means located on the blade 11 and on the insertion housing 12. According to one embodiment, the insertion housing 12 comprises at least one male blocking means 120 cooperating with at least one female blocking means 110 of the blade 11. Said male blocking means 120 may be a projection or a pin and said at least one female blocking means 110 may be a through hole. According to one embodiment, the insertion housing 12 comprises at least one female blocking means 110 cooperating with at least one male blocking means 120 of the blade 11.

In an advantageous manner, the blade assembly 10 can correspond to blades 11 of different sizes, according to the anatomy and the physical development of the subject. By means of a non-limiting example, the length of the blade 11, calculated as the distance between the distal tip 16 of the blade and an opposite proximal end of the blade along a direction perpendicular to the axis A, may be in the range from 80 mm to 159 mm. The blade 11 may be curved has shown in FIGS. 5 and 6, or straight to be adapted to different intubation procedure techniques or to adapt to the different anatomies of subjects. The blade 11 may be made of, or may comprise, a reusable material such as for example a metal; or alternatively the blade 11 may be made of, or may comprise, a disposable polymer or plastic, or any material known in the art.

According to one embodiment, the blade 11 may be made of, or may comprise, a metal and a plastic.

According to one embodiment, the blade 11 may be made of, or may comprise, a resilient elastically deformable material.

According to one embodiment, the metal is preferably stainless steel.

According to one embodiment, the polymer or plastic is preferably polycarbonate, acrylonitrile butadiene styrene (ABS) or polyamide.

According to one embodiment, the blade 11 is reusable and configured to be sterilized.

The distance between the engaging element 13 and said distal tip 16 of the blade 11 is configured to ensure that said distance is constant.

The laryngoscope device 1 is configured to be fixed to blade assemblies 10 which can mount or correspond to different blade sizes.

Figure 3:
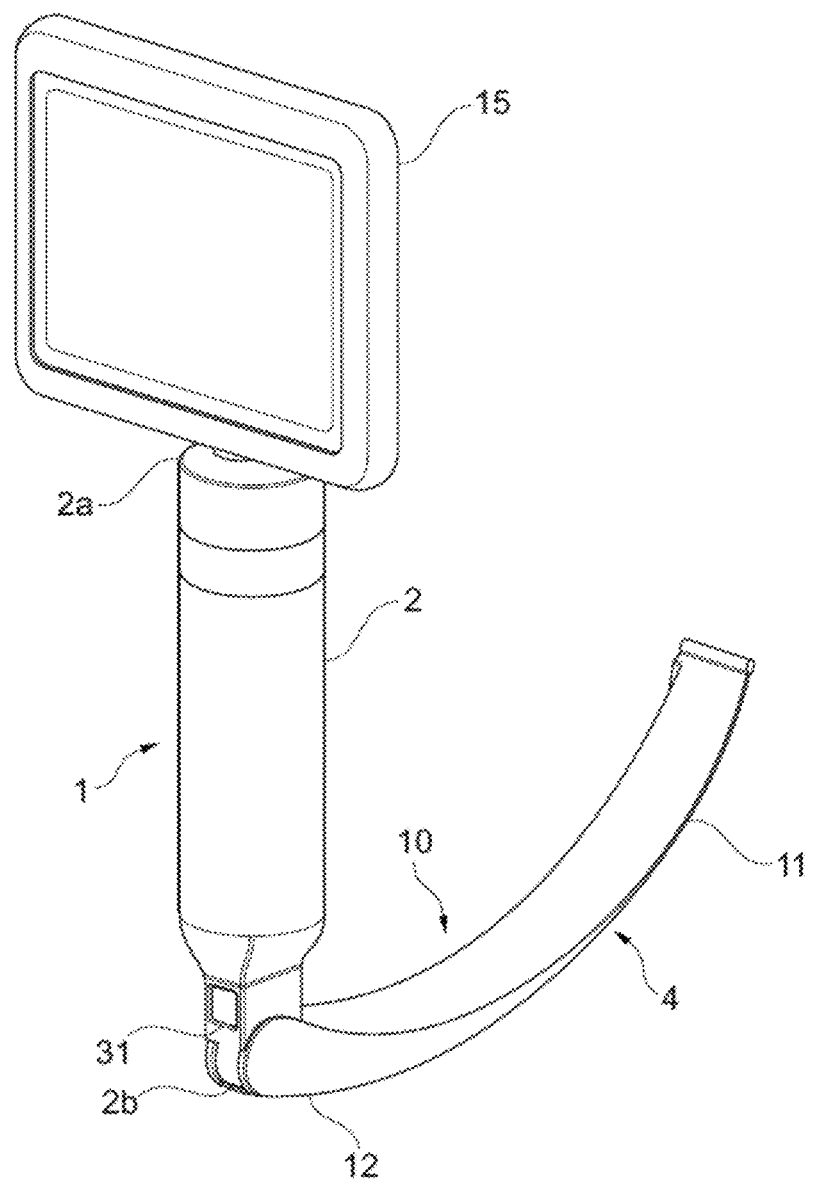
FIG. 3 is a perspective view according to another angle of the laryngoscope system of FIG. 1.

FIGS. 2 and 3 show a laryngoscope device 1 according to one embodiment of the present invention. According to this embodiment, the laryngoscope device 1 comprises a handle member 2, which makes it easier for a physician to manipulate the laryngoscope device. In the illustrated example, the handle member 2 comprises a cylindrical body extending along a longitudinal axis A and comprises a first portion 2a and an opposite second portion 2b. The proximal portion 2b of the handle member 2 comprises a retaining mechanism 3.

A power source is housed within the handle member 2. The power source may be one or more batteries. These batteries may be disposable, thereby necessitating an access door or hatch in the handle member. Access doors such as slidably removable doors can be constructed in a variety of configurations. Additionally, the batteries may be rechargeable. In such an embodiment, the handle member may further comprise a DC power port, a USB port, or the like.

The laryngoscope device 1 also comprises a display screen 15 assembled to the distal portion 2a of the handle member 2. The display screen 15 may be detachably assembled to the handle member 2 or integral with the handle member 2. The display screen 15 may be any suitable display such as LCD, or the like. Electrical and processing components necessary to convert data captured by an imaging device into on-screen visual output are known by those skilled in the art of medical device engineering; therefore, such details will not be discussed herein.

Figure 4:
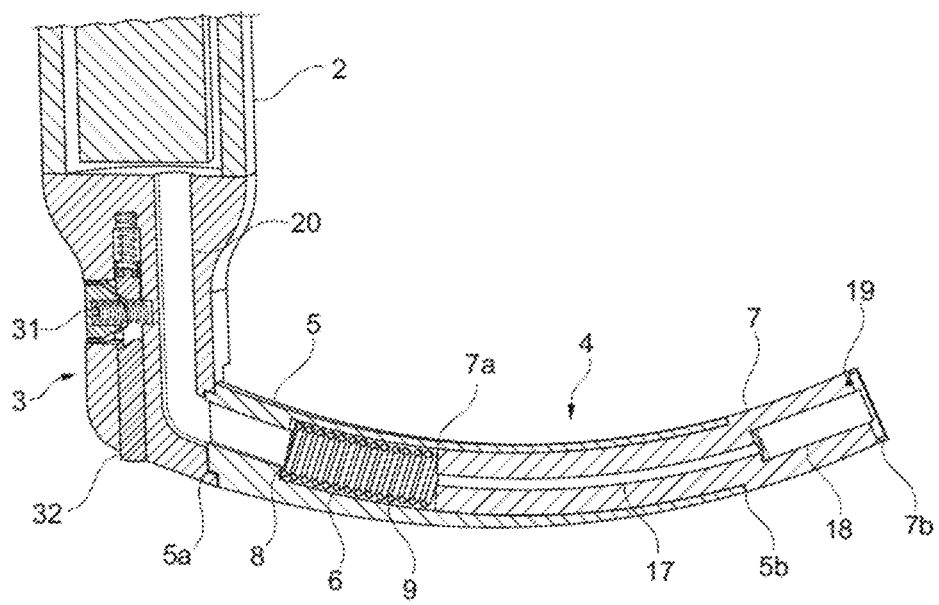
FIG. 4 is a cross section at a larger scale of the laryngoscope device of the laryngoscope system of FIG. 1.
Figure 5:
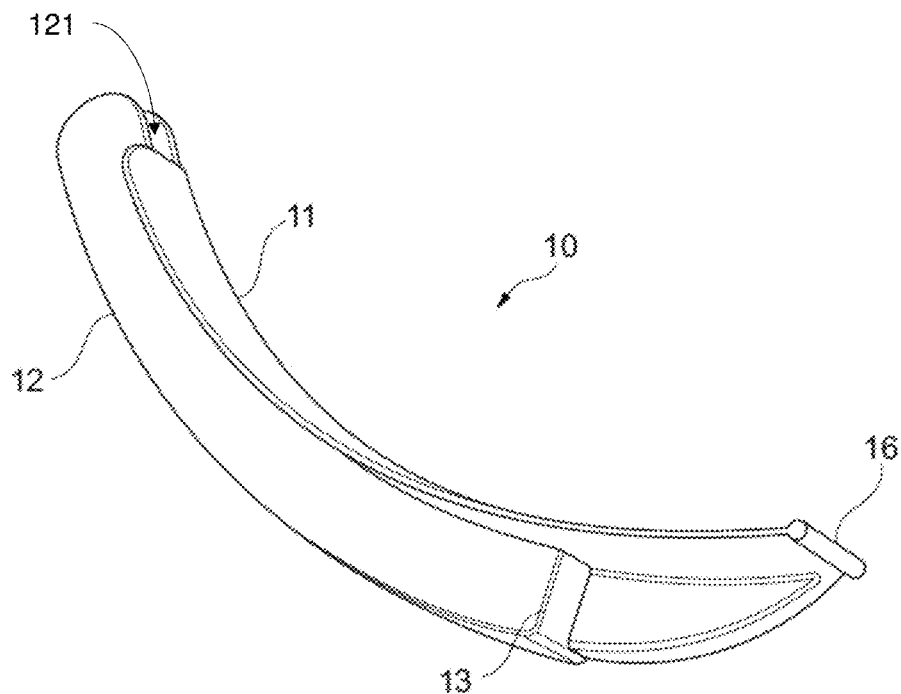
FIG. 5 is a perspective view of the blade assembly of the laryngoscope system of FIG. 1, comprising a blade and an insertion housing assembled together.

The laryngoscope device 1 comprises a front-end member 4 forming a frame protruding from the second portion 2b of the handle member 2. With reference to FIGS. 1 and 4, the front-end member 4 comprises two elements, i.e. a longitudinal member 5 and a sliding part 7.

The longitudinal member 5 has a proximal end 5a and a distal end 5b. The proximal end 5a of the longitudinal member 5 is integral with the second portion 2b of the handle member 2. Alternatively, the longitudinal member 5 may be mechanically coupled in a movable way to the handle member 2. The longitudinal member 5 comprises a channel 6 extending from the proximal end 5a of the longitudinal member to the distal end 5b of the longitudinal member. The cross section of the channel 6 may be circular or square or of any other shape known by those skilled in the art. The cross section dimensions of the channel 6 may vary along the longitudinal direction of the longitudinal member 5. The cross section of the channel 6 varies in such a way that it creates an abutment 8 in the channel 6. The longitudinal member 5 may be made of metal. The handle member 2 further comprises a handle channel 20 extending through the handle member 2 along the axis A and configured to be in communication with the channel 6 of the longitudinal member 5.

The sliding part 7 includes a body configured to be at least partially inserted in the channel 6 and movable along said channel 6. The sliding part 7 comprises a proximal end 7a and a distal end 7b. According to one embodiment, the cross-section shape and dimensions of the sliding part 7 are substantially equal to those of the internal walls of the channel 6. The cross-section dimensions of the sliding part 7 may increase at the sliding part distal portion so as to prevent the sliding part 7 from being completely inserted in the channel 6. The sliding part 7 comprises a transparent distal end 7b in order to protect the imaging device and light source from mechanical stresses.

The distal end 7b of the sliding part 7 comprises an imaging device 18 and a light source 19. The imaging device 18 may be a camera comprising an imaging sensor and one or more lenses. The light source 19 may be a LED or any other light source known by those skilled in the art. According to one embodiment, the imaging device 18 captures visual data of the area surrounding the blade distal tip 16 that are transmitted to the display screen 15 to which the imaging device 18 is connected. In this way, medical professionals can monitor the progress of a procedure via the display screen 15.

In the illustrated embodiment, the laryngoscope is a video laryngoscope. In this embodiment, video means such as a video camera is embedded in the laryngoscope of the invention, and coupled to display means.

The sliding part 7 comprises a lumen 17 extending from the proximal end 7a to the distal end 7b of the sliding part 7. Said lumen 17 is connected to the channel 6 and the handle channel 20. The handle channel 20 comprises a cavity to lodge electrical wires and/or optical wires (not shown) used to power the imaging device 18 and to transmit the electrical signals to the light source 19. Furthermore, the electrical wires or the optical wires make it possible to receive images to be displayed on the display screen 15.

The channel 6 further comprises a positioning spring 9 positioned between the abutment 8 and the proximal end of the sliding part 7. The positioning spring 9 has transversal dimensions inferior to the transversal dimensions of the channel 6 after the abutment 8. The positioning spring 9 may be a coil spring, a volute spring, a wave spring, or the like. The positioning spring 9 may be made of various elastic materials such as spring steel, annealed steel, non-ferrous metals, or the like.

The positioning spring 9 makes it possible to place the distal end of the sliding part 7b in contact with the engaging element 13 independently from the length between the complementary retaining means 14 of the insertion housing 12 and the engaging element 13.

The positioning spring 9 is compressed by the proximal end of the sliding part 7b when the complementary retaining means 14 is engaged with the retaining mechanism 3 of the laryngoscope device 1, thus locking the blade assembly 10 to the handle member 2.

The retaining mechanism 3, more clearly visible in FIGS. 7 and 8, is located in the second portion 2b of the handle member 2. The retaining mechanism 3 comprises a follower 32 movable so as to lock and unlock the blade assembly 10, the unlocking of the follower 32 being activated by a mechanical interface 33. The retaining mechanism 3 comprises a cam 31 and the follower 32, as shown in FIGS. 7 and 8.

In the illustrated embodiment, the cam 31 slides along a direction perpendicular to the axis A. The cam 31 can comprise a first elastic portion 34, which may be a spring, mechanically coupled to a mechanical interface 33 such as, for example, a badge.

The cam 31 and the follower 32 are arranged so that a movement of the cam 31 in a direction perpendicular to the axis A causes a movement of the follower 32 along the axis A.

According to one embodiment, the follower 32 cooperates with the complementary retaining means 14 of the insertion housing 12 so as to lock the blade assembly 10 with respect to the handle member 2. The follower 32 comprises a distal end 32a and a proximal end 32b. The proximal end 32b of the follower is configured to match and engage at least partially the complementary retaining means 14. The distal part 32a of the follower 32 may be mechanically coupled to a second elastic portion 35, such as for example a spring, which is aligned along the axis A so as to push the follower 32 into the female retaining means 14.

The cam 31 causes the follower 32 to move along the longitudinal axis A towards the distal end 2a of the handle member 2, so as to disengage the complementary retaining means 14 and unlock the insertion housing 12 from the handle member 2. In this embodiment, the second elastic portion 35 is compressed when the follower 32 moves along the longitudinal axis A towards the distal end 2a of the handle member 2.

The distance between the distal end 7b of the sliding part 7 and the distal tip 16 of the blade 11 is independent from the length of the blade 11. According to one embodiment, the engaging element 13 at the distal end 7b of the insertion housing 7 makes it possible to place the imaging device 18 and the light source 19 in proximity of the distal tip 16 of the blade 11, preferably in a location allowing to optimize the field of view of the imaging device.

The laryngoscope system according to the invention comprises the blade assembly 10 and the laryngoscope device 1 as described above.

The engaging element 13 of the laryngoscope device 1 induces a movement of the imaging device 18 by pushing the distal end 7b of the sliding part 7 of the laryngoscope device. In this case, the engaging element 13 generates on the distal end 7b a force opposite to the force generated by the positioning spring 9. This opposite force guaranties a safe locking of the complementary retaining means 14 in the retaining mechanism 3.

While various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A laryngoscope system, comprising:
   a laryngoscope device comprising:

a handle member;

a front-end member protruding from a proximal end of the handle member towards a distal end, wherein the front-end member comprises:

a longitudinal member connected with the handle member, the longitudinal member comprising a channel extending from the handle member to a distal end of the longitudinal member, a sliding part being configured to be at least partially inserted in the channel and movable along said channel, the channel comprising an abutment and a positioning spring between said abutment and a proximal end of the sliding part;

a blade assembly configured to cooperate with the front-end member of the laryngoscope device, the blade assembly comprising, fixed to one another:

a blade comprising a distal tip;

an insertion housing comprising a cavity configured to receive the front-end member of the laryngoscope device;

wherein the insertion housing includes an engaging element having an edge configured to cooperate with the distal end of the front-end member, the edge of the engaging element being positioned at a predefined distance from the distal tip of the blade.

2. The laryngoscope system according to claim 1, wherein, in the assembled configuration of the laryngoscope device and the blade assembly, the edge of the engaging element receives the distal end of the sliding part in abutment against the force generated by the positioning spring.

3. The laryngoscope system according to claim 1, wherein the sliding part comprises at a distal end an imaging device.

4. The laryngoscope system according to claim 1, wherein the sliding part comprises at a distal end a lighting device.

5. The laryngoscope system according to claim 1, wherein the sliding part comprises an imaging device at its distal end, the predefined distance between the engaging element and the distal tip of the blade allowing the imaging device to have a field of view that allows imaging.

6. The laryngoscope system according to claim 1, wherein the engaging element is transparent.

7. The laryngoscope system according to claim 1, comprising at least two blade assemblies having blades of different lengths.

8. The laryngoscope system according to claim 7, wherein, for the at least two blade assemblies, the predefined distance between the engaging element and the distal tip of the blade is the same, independently from the length of the blade.

9. The laryngoscope system according to claim 1, wherein the insertion housing of the blade assembly comprises retaining means configured to cooperate with a retaining mechanism of the laryngoscope device so as to lock the blade assembly with respect to the laryngoscope device.

10. The laryngoscope system according to claim 9, wherein the retaining mechanism of the laryngoscope device comprises a follower movable between a locking position, in which the follower locks the blade assembly with respect to the laryngoscope device, and an unlocking position, in which the follower unlocks the blade assembly with respect to the laryngoscope device, the transition between the locking position and the unlocking position of the follower being activated by a mechanical interface.

11. The laryngoscope system according to claim 10, wherein a movement of the mechanical interface in a first direction induces a movement of the follower in a second direction perpendicular to the first direction.

12. The laryngoscope system according to claim 1, wherein the sliding part comprises an imaging device at its distal end, the laryngoscope system further comprising a display screen assembled to a distal end of the handle member and connected to the imaging device.

13. The laryngoscope system according to claim 1, wherein the blade and the insertion housing of the blade assembly are fixed to one another by fixation configured to block at least one degree of freedom of the blade relative to the insertion housing.

* * * * *